United States Patent [19]
Beplate

[11] Patent Number: 5,370,632
[45] Date of Patent: Dec. 6, 1994

[54] DIAPER WITH INTEGRAL OVERFLOW RESERVOIR

[76] Inventor: Douglas K. Beplate, P.O. Box 141, Potlatch, Id. 83855

[21] Appl. No.: 54,905

[22] Filed: Apr. 29, 1993

Related U.S. Application Data

[60] Continuation-in-part of Ser. No. 846,516, Mar. 4, 1992, abandoned, which is a division of Ser. No. 650,927, Feb. 5, 1991, abandoned.

[51] Int. Cl.$^5$ .............................................. A61F 13/15
[52] U.S. Cl. .................................. 604/385.1; 604/378
[58] Field of Search .............................. 604/385.1, 378

[56] References Cited

U.S. PATENT DOCUMENTS

| 4,950,262 | 8/1990 | Takagi | 604/385.1 |
| 5,176,671 | 1/1993 | Roessler et al. | 604/386 |
| 5,221,277 | 6/1993 | Beplate | 604/385.1 |

FOREIGN PATENT DOCUMENTS

| 498612 | 8/1992 | European Pat. Off. | 604/385.1 |
| 2561078 | 9/1985 | France | 604/385.1 |

Primary Examiner—Jerome L. Kruter
Attorney, Agent, or Firm—J. Winslow Young

[57] ABSTRACT

A diaper having an inner panty enclosed in spaced relationship by an outer panty. An absorbent pad is inserted in an opening in the inner panty. The inner panty holds the absorbent pad snugly against the perineal region between the legs of the wearer. An outer panty is secured around its periphery to the inner panty. The spaced relationship between the outer panty and the inner panty forms an overflow reservoir for the absorbent pad.

6 Claims, 4 Drawing Sheets

DIAPER WITH INTEGRAL OVERFLOW RESERVOIR

RELATED APPLICATIONS

This application is a continuation-in-part application of my copending application Ser. No. 07/846,516 filed Mar. 4, 1992 for REUSABLE DIAPER AND METHOD now abandoned which is a divisional of Ser. No. 07/650,927 filed Feb. 5, 1991 for REUSABLE DIAPER AND METHOD (now abandoned).

BACKGROUND

1. Field of the Invention

This invention relates to diapers and, more particularly, to a novel diaper having an absorbent pad suspended between the legs of a wearer and surrounded exteriorly by an overflow reservoir.

2. The Prior Art

Diapers of one form or another have been known for many generations and are generally defined as a basic garment for infants and incontinent adults. A conventional diaper consists of a folded cloth or other absorbent material drawn up between the legs and fastened about the waist of the wearer. Historically, diapers were available in the form of a layer of cloth about one meter square. To produce a suitable diaper, the cloth was folded in any one of plurality of patterns to achieve the appropriate diaper size and then pinned with safety pins about the waist of the wearer. This entire process is fraught with problems not only in folding the diaper to the wrong size but also in injuries resulting from accidental punctures from the safety pin. By their very nature, cloth diapers require the use of a separate, water-repellant cover to resist leakage of urine or even watery feces through the cloth fabric.

The result of the foregoing is that within the past few decades there has been an explosive increase in the use of disposable diapers in both the pediatric and the adult settings. User convenience along with the aesthetics of disposability have been the primary driving forces behind the wide acceptance of disposable diapers. While convenient, disposable diapers represent not only a significant increase in cost but, more importantly, represent a major concern environmentally in that they constitute a significant portion of the solid waste stream. This, in turn, means that a significant portion of the landfill space is occupied by disposable diapers. Further, since a significant number of the disposable diapers contain feces, they also represent a threat to the environment through fecal contamination particularly due to the pathogens carried in most feces. One of the principal advantages to the use of cloth diapers is the fact that the human wastes are directed into the sewer system where it is properly treated.

Shulman (U.S. Pat. No. 2,664,895) discloses a waterproof diaper having a pocket to hold the absorbent pad.

Deutz (U.S. Pat. No. 2,828,745) discloses a diaper-like construction having a water-proof material as an outer covering and a plurality of superposed layers of absorbent sheet material such as flannel secured to the outer layer. A peripheral channel 28 is designed to receive any excess overflow to keep it from escaping the garment.

Niolon (U.S. Pat. No. 2,494,307) discloses an inversive fold diaper fabricated from cloth and is particularly characterized by being free from attaching devices.

Papajohn (U.S. Pat. No. 4,044,769) discloses a panty with a sanitary napkin holder. A fluid-tight compartment removably receives therein the sanitary napkin in fluid-tight relationship.

Repke et al (U.S. Pat. No. 4,205,679) disclose a unitary, multi-layer disposable undergarment for use in training infants. The garment is constructed from a non-woven, stretchable fabric and includes an absorbent inner ply and a moisture-impervious outer ply. Longitudinal micropleats provide the material with its stretchability.

Pigneul et al (U.S. Pat. No. 4,617,022) disclose a disposable diaper having a rectangular shaped absorbent pad covered on a portion of its internal surface and its external surface with a sheet of liquid impermeable material such as polyethylene.

Hults et al (U.S. Pat. No. 4,671,793) disclose a disposable training pant having a plastic outer cover and an inner absorbent liner that is thin at the sides and thick in the middle crotch area from front to back.

Suzuki et al (U.S. Pat. No. 4,892,528) disclose a disposable diaper having an absorbent core, a water-permeable topsheet and a water-impervious backsheet held against the bottom surface of the absorbent core.

Cottenden (U.S. Pat. No. 4,898,594) discloses an incontinent device having a sewn in absorbent pad. A sheet of liquid-impervious material is interposed between the garment and the outer surface of the pad, the outer surface being defined as the surface of the pad facing away from the patient. First and second stitching are used to prevent the capillary flow of liquid from escaping the absorbent pad through the stitching.

Douglas, Sr. (U.S. Pat. No. 4,909,804) discloses a child's toilet training pants having an outer, plastic, waterproof sheet and a coextensive inner sheet of soft material to be worn against the skin. An intermediate strip of highly water absorbent material is placed to be worn between the legs.

Nathan (U.S. Pat. No. 4,928,323) discloses a garment having a plurality of panels attached to the crotch piece to form inner and outer pairs of pockets. Disposable absorbent pads such as sanitary napkins are supported in the pockets.

Takagi (U.S. Pat. No. 4,950,262) discloses a collection device for the collection of bodily excretion. A bellows-like chamber below an absorbent pad expands to receive the excretions therein. This device is essentially a bedpan with an absorbent pad inside the bedpan.

Stanton (U.S. Pat. No. 5,005,525) discloses an animal-mountable control device for absorbing urine excreted by a male dog to prevent the male dog from marking an object with urine. An absorbent pad is enclosed in a pouch strapped to the body of the dog.

Anderson (U.S. Pat. No. 5,062,839) discloses a disposable training panty having a permeable outer covering and an inner absorbent portion secured to the outer covering. The permeable outer covering allows wetness to quickly cool the panty causing the child discomfort as a means for potty training the child.

Wippler et al (U.S. Pat. No. 5,069,672) disclose a reusable diaper having inner and outer layers of absorbent material with a liquid-impervious layer between the inner and outer layers. Pockets at each end of the crotch piece receive the respective ends of the diaper therein to hold it in place.

Davis (U.S. Pat. No. 5,074,84) discloses a disposable undergarment having at least one breakaway panel. The breakaway panel is designed to allow the user to remove the undergarment without sliding the undergarment down the length of both legs.

Henry (U.S. Pat. No. 5,106,382) discloses a washable diaper with a fixed waterproof cover. The diaper includes an inner layer formed at least partially of a moisture absorbent textile fabric while the outer layer is formed of a water resistant fabric.

Fahrenkrug et al (U.S. Pat. No. 5,135,522) disclose a diaper having a rectangular disposable chassis assembly and a reusable elasticized cloth belt to hold the diaper against the body during use. The core of the diaper contains a lower pledget with hydrogel that swells outwardly when wetted.

Coates (U.S. Pat. No. 5,137,526) discloses a reusable diaper having a fluid absorbent pad on the inner surface of a waterproof, hourglass-shaped, diaper shell. The absorbent pad may be sewn into the shell or be floating in the shell between the leg holes of the diaper.

Clearly, each prior art system of diapers has its advantages and disadvantages. Accordingly, it would be a significant advancement in the art to provide a method for a diaper that incorporates the advantages from each system. It would also be an advancement in the art to provide a reusable diaper that is prefolded and includes a water-resistant outer shell. Another advancement in the art would be to provide a diaper that supports an absorbent pad snugly between the legs of the wearer. Another advancement would be to provide an overflow reservoir below the absorbent pad of the diaper. Such a novel diaper and method is disclosed and claimed herein.

BRIEF SUMMARY AND OBJECTS OF THE INVENTION

This invention relates to a reusable diaper having an absorbent, cloth-covered pad suspended in an inner shell, the absorbent pad being enclosed in an outer, water-resistant shell. The water-resistant outer shell forms an overflow reservoir by enclosing the inner shell in spaced relationship while the inner shell suspends the absorbent pad snugly between the legs of the wearer. The inner shell in the region of the absorbent pad is in fluid communication with the overflow reservoir which is the spacial separation between the inner shell and the outer shell to allow surplus liquid to pass into this space. The inner shell also supports the absorbent pad in the extended configuration to resist its bunching during periods of wear. The absorbent pad is confined to the area between the legs of the wearer to preclude its bulk from extending to the external profile of the wearer. A hook and hoop fastener system fastens the diaper about the waist of the wearer. Elasticized sections at each side of the diaper provide a snug fit around the legs of the wearer.

It is, therefore, a primary object of this invention to provide improvements in reusable diapers.

Another object of this invention is to provide a reusable diaper characterized by the absence of absorbent material on the external profile of the legs of the wearer.

Another object of this invention is to provide improvements in the method of providing a diaper.

Another object of this invention is to provide a reusable diaper having an absorbent pad incorporated into an inner shell with the inner shell enclosed in a water-resistant, outer shell, the outer shell forming an overflow reservoir below the absorbent pad.

Another object of this invention is to provide a reusable diaper having an absorbent pad supported snugly between the legs of a wearer, the absorbent pad being held against twisting or bunching while being held snugly between the legs of the wearer.

Another object of this invention is to provide a reusable diaper having a hook and loop fastener system for adjustably fastening the diaper about the waist of the wearer.

These and other objects and features of this invention will become more readily apparent from the following description, the accompanying drawing and the appended claims.

DETAILED DESCRIPTION OF THE PREFERRED EMBODIMENT

Figure 1:
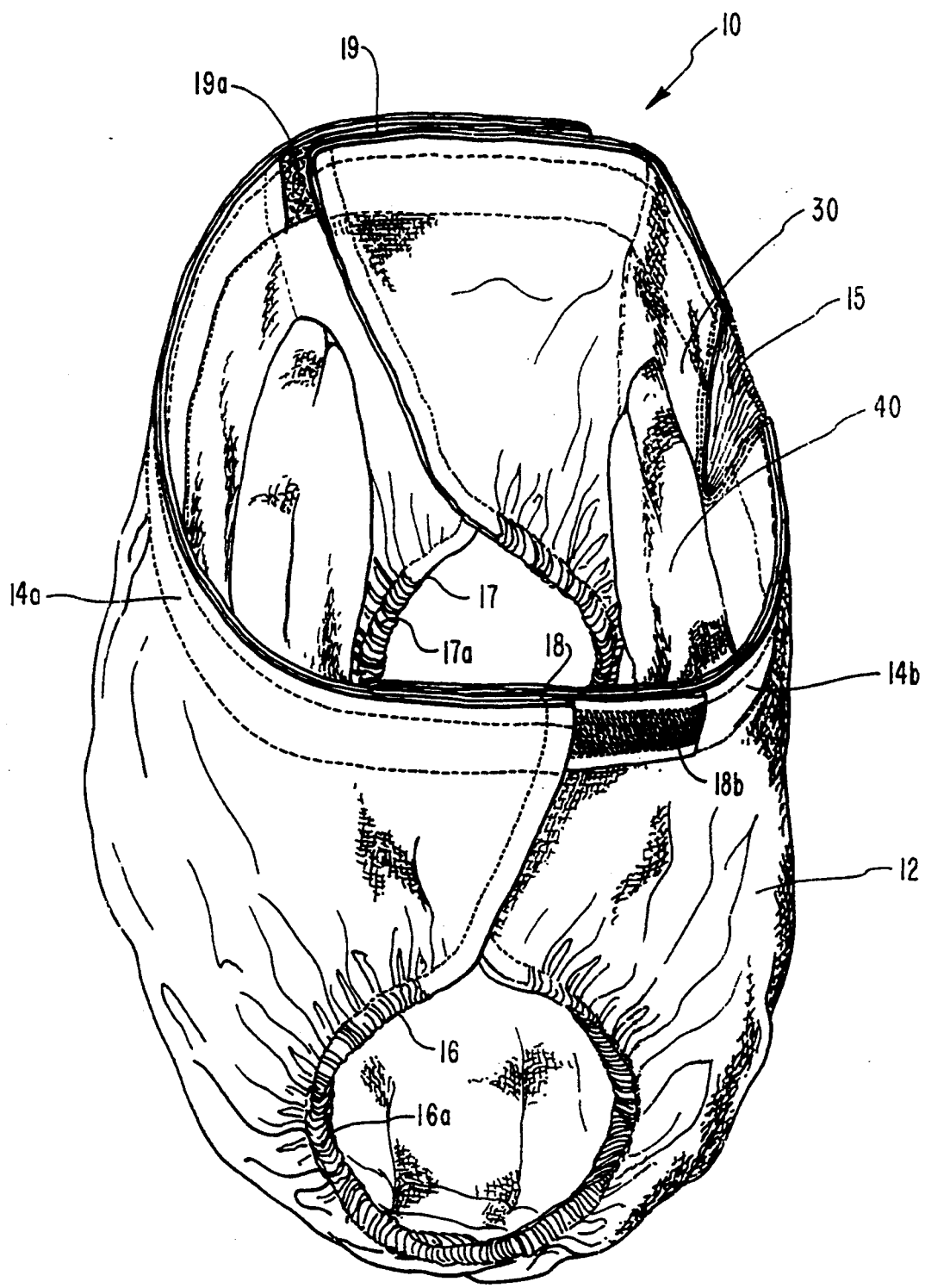
FIG. 1 is a perspective view of the novel diaper of this invention.

The invention is best understood from the following description with reference to the accompanying drawing wherein like parts are designated by like numerals throughout.

General Discussion

Diapers are important not only for the pediatric population but also for certain segments of the adult population. The term "diaper" is used herein in a generic sense for any absorbent-type undergarment worn for the catchment and containment of urine and/or feces. The need for diapers among the pediatric population is accepted knowledge and is due to the fact that in practically all cases of pediatric diaper usage, the diaper is a temporary (up to three or four years) measure until the wearer's physiological maturity progresses sufficiently to the point where the normal excretory functions can be controlled voluntarily. The term "pediatric population" is usually understood to mean those persons up to about three or four years of chronological age and a weight up to about 40 pounds (18 kilograms). The term "adult population" is used herein to describe all other persons who may require the use of a diaper either in an acute sense or a chronic sense.

Usage of diapers by the adult population is generally the result of enuresis, injuries, mental and/or physical deterioration, disease, confinement, incontinence, and the like, regardless of the origin of the particular problem. For instance, many women suffer from certain forms of urinary incontinence due to injuries inflicted on the bladder sphincter during childbirth. Physical incapacity as well as mental dementia, particularly among the geriatric portion of the adult population, appears to be the major factor necessitating the use of diapers among this population. In either circumstance, it is important for the wearer that the diaper should be easily donned either by the wearer or another person and changeable with equal facility.

Advantageously, the novel diaper of this invention is configured with an absorbent pad that is held snugly in spaced relationship between the legs of the wearer. The diaper is, therefore, particularly characterized by the absence of any portion of the absorbent pad being found on the outside profile of the legs. This means that, unlike prior art, reusable diapers, there is no extraneous bulk around the waist or legs of the wearer to reveal to the casual observer that the wearer is wearing a diaper. Not only does this feature enable the ambulatory wearer to wear the diaper of this invention under normal clothing but it also significantly enhances the self esteem of the wearer by the knowledge that the presence of a diaper on the wearer is effectively hidden from accidental discovery or observation.

Another distinct advantage of the novel diaper of this invention is that it includes an overflow reservoir below the absorbent pad, the overflow reservoir being formed from the spatial relationship between the external, water resistant outer panty and the absorbent pad. Further, since the absorbent pad is suspended in the inner panty and the portion of the inner panty supporting the absorbent pad is also fabricated from a water resistant material, the overflow reservoir is essentially a waterproof reservoir with the exception of the absorbent pad which forms the ingress for liquid into the overflow reservoir.

Detailed Description

Referring now more particularly to FIG. 1, the novel, reusable diaper of this invention is shown generally at 10 and includes an outer panty 12 and an inner panty 30 with the inner panty 30 supporting an absorbent pad 40 in spaced relationship inside the outer panty 12. Reusable diaper 10 is configured with a panty-like external profile with a waist band 14 separated into a front waist band 14a and a rear waist band 14b. Front waist band 14a is configured to be releasably joined to rear waist band 14b at each side of reusable diaper 10 above leg openings 16 and 17. Leg opening 16 is designed as an opening for the left leg of a wearer (not shown) and includes an elasticized segment 16a to assure a snug fit about the leg (not shown) while leg opening 17 is correspondingly configured with an elasticized segment 17a to accommodate the right leg of the wearer (not shown) in a snug-fitting relationship.

The releasable joinder of the ends of front waist band 14a to the respective ends of rear waist band 14b is accomplished using matching pairs of hook and loop fastener systems 18 and 19. Loop portions 18a and 19a of hook and loop fastener systems 18 and 19, respectively, are attached at each end of front waist band 14a while hook portion 18b and hook portion 19b (FIG. 4) are attached at each end and on the outside face of rear waist band 14b. This particular orientation of the respective hook and loop portions of hook and loop fasteners 18 and 19 is important due to the inherent nature of commercially available hook and loop fastener systems. In particular, the loop portion is generally configured with a relatively soft, felt-like texture whereas the hook portion is specifically designed with a certain degree of stiffness to enable the hooks therein to suitably penetrate the loops so as to releasably engage the same. Such hook and loop fastener systems are widely available commercially from Velcro, Inc., Manchester, N.H., under their trademark, VELCRO. In view of the relatively soft, felt-like texture of loop portions 18a (FIGS. 2-4) and 19a, they are placed on the inner face of front waist band 14a where any exposed portions thereof (as shown in FIG. 1 by loop portion 19a) are placed in contact with the wearer (not shown). It is particularly important that hook portions 18b and 19b (FIG. 4) are placed on the outside face of rear waist band 14b so as to minimize contact by the wearer (not shown).

At this point of the description of the various features included in reusable diaper 10, it should be pointed out that even though reusable diaper 10 is intended to be fully reusable, the same, novel features can be incorporated, advantageously, into a diaper 10 that is entirely disposable. As such, diaper 10 provides significant advantages in that the total bulk thereof as the result of the overall size and placement of absorbent pad 40 is substantially reduced as compared to a commercially available, disposable diaper (not shown). In particular, absorbent pad 40 as well as inner panty 30 and outer panty 14 can be fabricated entirely from materials acceptable as solid wastes and, as such, would provide significant advantages since the overall bulk of absorbent pad 40 is substantially less than the conventional, commercially available, disposable diaper (not shown).

The back of reusable diaper 10 includes an elastic gore 15 of an elastic fabric inserted in the center of rear waist band 14b. Elastic gore 15 is designed to enhance the fit of waist band 14 about the waist of a wearer (not shown) by providing a limited degree of elasticity to waist band 14. This amount of elasticity is sufficiently to adapt waist band 14 to changes to the circumference of waist of the wearer (not shown) during movement, changes in posture, breathing, and the like.

Figure 2:
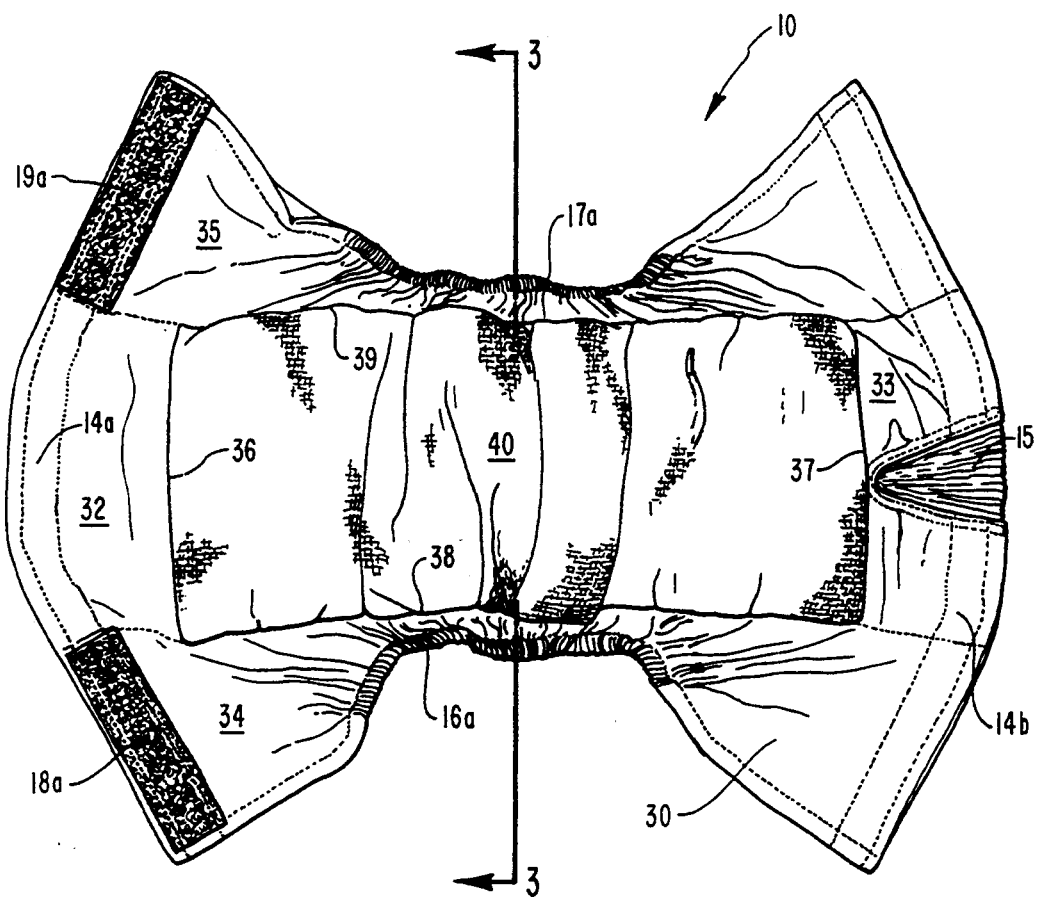
FIG. 2 is a plan view of the novel diaper shown in FIG. 1 but with the diaper opened.

Referring now also to FIG. 2, inner panty 30 generally conforms to the external profile of outer panty 12 but is assembled from a front panel 32, a rear panel 33, a left panel 34, and a right panel 35. Front panel 32 is joined to a front end of absorbent pad 40 along a seam 36 while rear panel 33 is joined to a rear end of absorbent pad 40 along a seam 37. Left panel 34 extends the full length of inner shell 30 and is joined along a seam 38 to a left edge of each of front panel 32, absorbent pad 40, and rear panel 33. Similarly, right panel 35 extends the full length of inner shell 30 and is joined along a seam 39 to the right side of each of front panel 32, absorbent pad 40, and rear panel 33.

Figure 3:
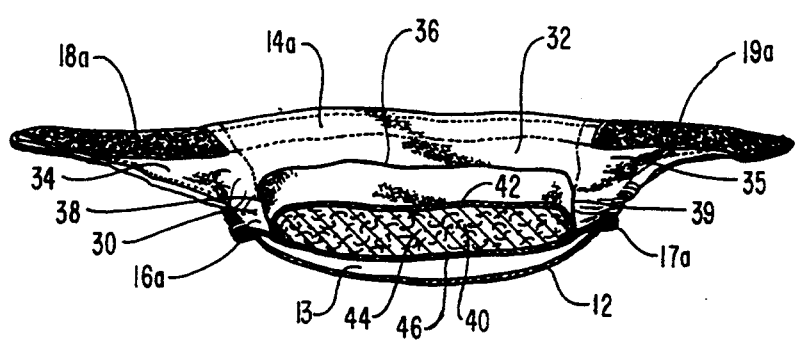
FIG. 3 is a cross sectional view taken along lines 3—3 of FIG. 2.

Inner panty 30 is designed to suspend absorbent pad 40 in spaced relationship between leg openings 16 and 17 (FIG. 1) and thereby suspend absorbent pad 40 snugly between the legs of the wearer (not shown) when waist band 14 is snugly engaged around the waist of the same. Further, inner panty 30 is also specifically configured to suspend absorbent pad 40 in spaced relationship within the profile of outer panty 12. With particular reference also to FIG. 3, absorbent pad 40 is shown in this cross sectional view as being suspended by inner panty 30 in spaced relationship to outer panty 12, the spatial separation therebetween being shown as overflow reservoir 13.

Overflow reservoir 13 is, therefore, defined as the spatial separation below absorbent pad 40 and is spatially defined by the outer panty 12 on the bottom and the corresponding portions of inner panty 30 circumscribing absorbent pad 40. Further, inner panty 30 and outer panty 12 are fabricated from a water resistant fabric so as to effectively isolate any surplus liquid (not shown) received into overflow reservoir 13 that has entered therein through absorbent pad 40. However, as the name implies, overflow reservoir 13 is configured for just that purpose, an overflow reservoir, so that its intended use is primarily one of handling "emergency" conditions rather than conditions encountered on a regular basis. Even under the so-called emergency conditions, overflow reservoir 13 is especially useful since it holds the surplus liquid away from the body and/or legs of the wearer (not shown).

Absorbent pad 40 is configured from an upper layer 42 and a lower layer 46 with a fibrous fill 44 therebetween. Upper layer 42 and lower layer 46 are fabricated from a soft fabric material such as a cotton flannel while fibrous fill 44 is selected from a nonwoven, batting-type material such as a polyester, or the like. In one presently preferred embodiment fibrous fill 44 was selected from a blended cotton and wool batting. Essentially, absorbent pad 40 is constructed as a small quilt or pillow whose primary function is the absorption and retention of liquids. Upper layer 42 is specifically directed to a soft, absorbent, nonallergenic material such as cotton flannel, since its primary function is to reside in contact with the perineal region of the wearer by being held snugly between the legs of a wearer where it can readily wick away any moisture deposited thereon. The moisture (not shown) is pulled directly into fiber fill 44 through this inherent wick action.

Overflow reservoir 13 is formed by outer panty 12 assuming a loose, slightly bouffant profile when inner panty 30 is secured to a wearer. Overflow reservoir 13 is particularly useful in the event excess liquid is deposited in absorbent pad 40. However, given the nature of absorbent pad 40 this eventuality is somewhat limited. For example, in one experimental test, over 280 milliliters of water were poured on and absorbed by absorbent pad 40 without any of the water passing into overflow reservoir 13. This particular experiment was conducted using a pediatric size, reusable diaper 10. The advantage of absorbent pad 40 in such a circumstance is more clearly understood when it is pointed out that a pediatric wearer (not shown) of reusable diaper 10 has normal bladder capacity of only about 85 milliliters.

Absorbent pad 40 performs another unique function when reusable diaper 10 is used in an adult setting. In particular, for those instances of bladder incontinence, the outflow of urine is more or less a constant drip generally at a rate that approximates the excretion of urine from the kidneys. In such circumstances, it is highly desirable for upper layer 42 to wick away this liquid directly into fiber fill 44. Absorbent pad 40 thereby quickly and efficiently retains the absorbed liquid while inner panty 30 suspends absorbent pad between leg openings 16 and 17. This feature is important since it effectively inhibits excess liquid in absorbent pad 40 from leaking out of either of leg openings 16 or 17.

Outer panty 12 and inner panty 30 are each fabricated from a water resistant fabric such as a nylon. This feature is important not only with respect to outer panty 12 and the fact that it creates overflow reservoir 13 as a spatial separation between inner panty 30 and outer panty 12, but also because it also effectively inhibits the migration or wick action of liquid from absorbent pad 40 through either of left panel 34 or right panel 35 to the respective leg openings, leg opening 16 or leg opening 17.

Figure 4:
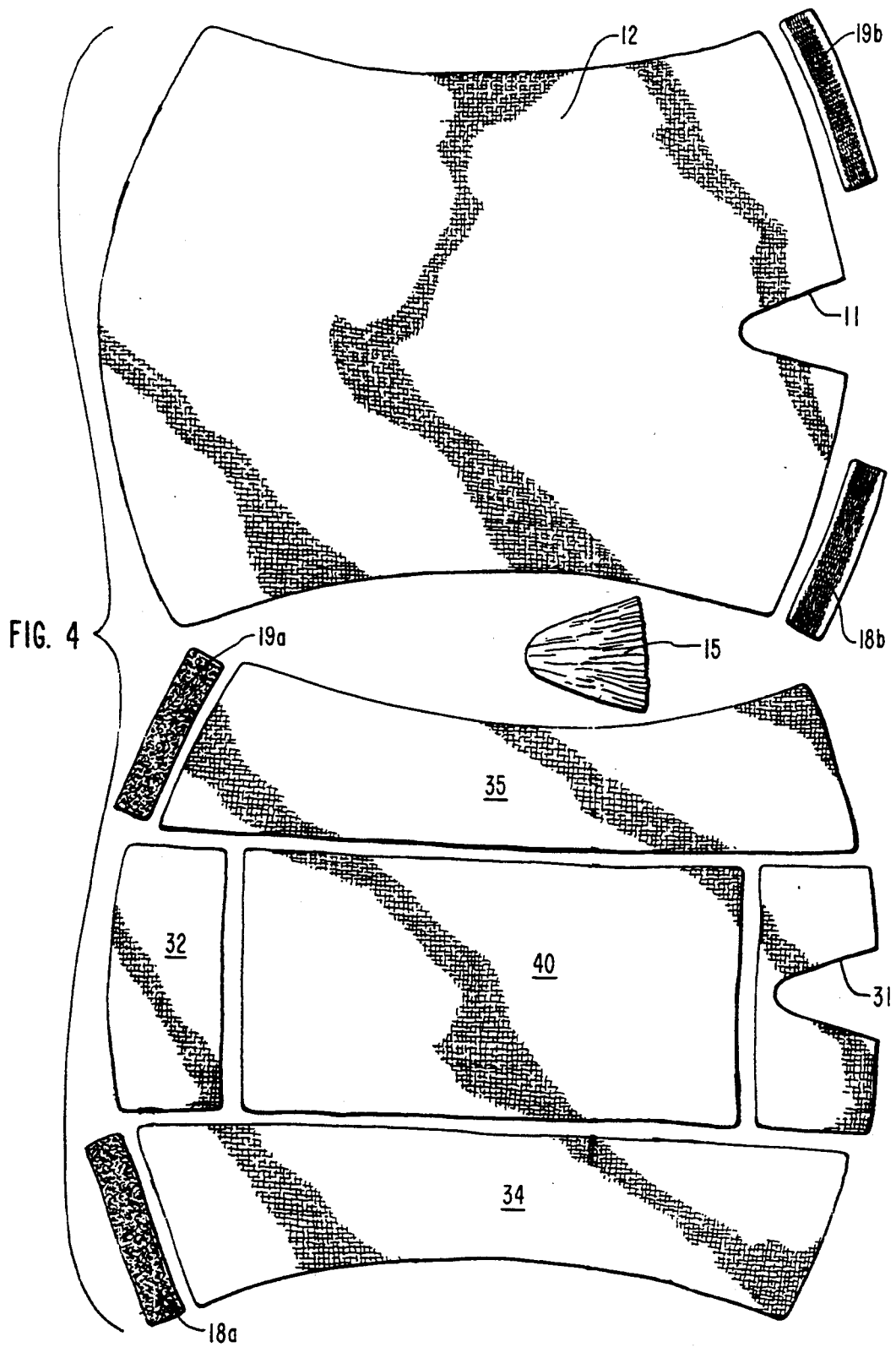
FIG. 4 is an exploded plan view of the various elements that are assembled into the diaper shown in FIG. 1.

With reference now to FIG. 4, outer panty 12 and inner panty 30 are shown in an exploded plan view of the various elements that are assembled to create reusable diaper 10. Outer panty 12 includes a cutout 11 adapted to receive elastic gore 15. A matching cutout 31 is also found in rear panel 33 and, when superimposed over cutout 11 conforms to the profile of elastic gore 15.

Figure 5:
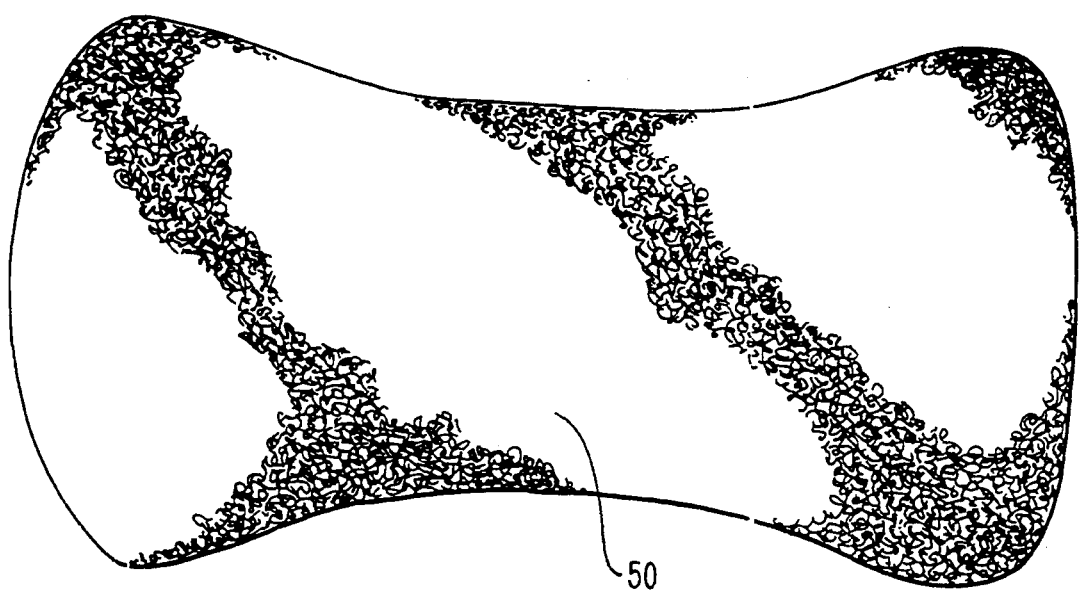
FIG. 5 is a plan view of the removable liner for the novel reusable diaper of this invention.

FIG. 5 shows a liner 50 that is adapted to be placed on top of absorbent pad 40 for the purpose of acting as a catchment for the solids part of feces excreted by the wearer (not shown) of reusable diaper 10. Liner 50 may be fabricated from a flannel cloth material with the intention of being either reusable or even disposable. As a reusable item, liner 50 significantly reduces handling problems when feces (not shown) is deposited thereon since it is a simple matter for the attendant (not shown) to simply grasp each end of liner 50 and transport it to the appropriate waste receptacle (not shown). As a disposable system, liner 50 is fabricated from a suitable fabric material commonly found in disposable diapers, for example, and deposited directly into a toilet for disposal.

The Method

Reusable diaper 10 is assembled with inner panty 30 enclosed in spaced relationship within outer panty 12. Absorbent pad 40 is suspended in inner panty 30 and is specially configured to be held snugly against the perineal region when suspended between the legs of the wearer (not shown). Inner panty 30 is configured with a modified hour glass-like outline as is outer panty 12 so as to readily adapt reusable diaper 10 to being worn between the legs of the wearer (not shown). Inner panty 30 is joined to outer panty 12 along their respective external perimeters so as to effectively enclose absorbent pad 40 inside the confines of outer panty 12. Importantly, absorbent pad 40 is not merely attached to an upper surface of inner panty 12 but is, in effect, inserted in an opening formed therein through the joinder of front panel 32 and rear panel 33 with each of left panel 34 and right panel 35. In this manner, excess liquid (not shown) received by absorbent pad 40 is free to enter overflow reservoir 13 thereby significantly reducing the possibility that the excess liquid could escape from either of leg openings 16 and 17. Clearly, if absorbent pad 40 were placed directly on top of a water-resistant fabric (such as if inner panty 30 were constructed similarly to outer panty 12) there would be a very high probability that the excess liquid (not shown) would leak out of either of leg openings 16 and 17.

Reusable diaper 10 is readily mounted and removed from about the waist of the wearer (not shown). Mounting is accomplished by bringing absorbent pad 40 upwardly between the legs into snug engagement with the perineal region and fastening waist band 14 about the waist. Hook and loop fasteners 18 and 19 each have sufficient length to accommodate adjustably securing waist band 14. Further, elastic gore 15 contributes a limited degree of elasticity to waist band 14 to accommodate changes in the circumference of waist band 14 during wear of reusable diaper 10.

Advantageously, since all of the bulk of absorbent pad 40 is held in spatial relationship between the legs, the only visible portion of reusable diaper 10 on the outside of the legs are the corresponding portions of inner panty 30 and outer panty 12. Accordingly, excessive bulk is utterly eliminated from those portions of reusable diaper 10 which would otherwise create an unsightly bulge seen under the outer clothing of the wearer. This is important particularly when reusable diaper 10 is configured as an undergarment for a member of the adult population.

Reusable diaper 10 is easily replaced by simply separating hook and loop fasteners 18 and 19 and removing absorbent pad 40 from between the legs of the wearer. Since the total bulk of reusable diaper 10 is substantially smaller than that of a conventional disposable diaper as well as a conventional reusable diaper, reusable diaper 10 is readily concealable (if necessary) for transportation to a place for washing the same. Further, any surplus liquid is overflow reservoir 13 is held there until reusable diaper 10 is subjected to the conventional washing cycle.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A diaper having an overflow reservoir comprising:
   an inner panty having a first, external periphery, a waist portion, an abdominal covering portion, a buttocks covering portion, and a crotch section, said panty being configured to be worn between the legs and about the waist of a wearer with the crotch section held snugly against the perineal region of the wearer;
   an open crotch panel in said crotch section, said crotch section comprising a first side panel on one side of said crotch section and a second side panel on the other side of said crotch section, said first and second side panels forming said open crotch panel in said crotch section and in spaced relationship between the legs of the wearer;
   an absorbent pad mounted in said open crotch panel of said inner panty;
   an outer panty having a second, external periphery and mounted to said inner panty by joinder of said second, external periphery of said outer panty to said first, external periphery of said inner panty; and
   an overflow reservoir between said absorbent pad and said outer panty, said outer panty being fabricated from a water resistant fabric and cooperatingly forming said overflow reservoir below said absorbent pad by extending outwardly away from said absorbent pad, said overflow reservoir thereby being defined by said first side panel and said second side panel in combination with said outer panty.

2. The diaper defined in claim 1 wherein said inner panty is fabricated from a water resistant fabric.

3. A diaper having an overflow reservoir and adapted to be worn by a wearer having a waist and legs comprising:
   an outer panty comprising a first external periphery, a front panel, a back panel, and a crotch panel, said outer panty configured to be worn between the legs of the wearer and comprising a waistband having a front waistband portion and a rear waistband portion, said waistband including hook and loop fastener means for adjustably securing said waistband portions together;
   an inner panty comprising a second external periphery which is secured to said first external periphery of said outer panty, said inner panty further comprising a waist band, a front panel, a rear panel, and a crotch portion;
   an elongated opening having a first perimeter and a first area in said crotch portion of said inner panty;
   an absorbent pad having a second perimeter and a second area and a shape and size generally corresponding to said elongated opening, and the second perimeter and second area being equal to or incrementally less than the first perimeter and first area, respectively, such that said absorbent pad is secured along said second perimeter in said elongated opening in said inner panty, said inner panty supporting said absorbent pad against the perineal region between the legs of the wearer; and
   an overflow reservoir between said absorbent pad and said outer panty.

4. The diaper defined in claim 3 wherein said crotch portion comprises a left side panel and a right side panel with said elongated opening between said left side panel and said right side panel, said left side panel and said right side panel holding said absorbent pad in spaced relationship between the legs of the wearer.

5. The diaper defined in claim 4 wherein said overflow reservoir is defined by said left side panel, said right side panel, and said outer panty, each of said left side panel, said right side panel and said outer panty being fabricated from a water resistant fabric.

6. A method for providing a diaper with an overflow reservoir comprising the steps of:
   preparing an absorbent pad to be worn between the legs of a wearer, said absorbent pad including an upper fabric layer, a lower fabric layer, and a fibrous fill between said upper fabric layer and said lower fabric layer;
   configuring an inner panty comprising a waistband, a front section, a back section and a crotch portion, said crotch portion having an elongated opening with dimensions corresponding to said absorbent pad;
   mounting said absorbent pad in said elongated opening in said inner panty;
   limiting the external periphery of said absorbent pad so as to preclude said absorbent pad from extending outwardly to the sides of said legs and fabricating said inner panty and said outer panty from a water resistant fabric thereby inhibiting wicking of liquid from said absorbent pad toward the legs of the wearer;
   forming an overflow reservoir below said absorbent pad by preparing an outer panty and enclosing said inner panty in said outer panty while holding said outer panty in spaced relationship to said inner panty and said absorbent pad;
   securing said inner panty to said outer panty along an external periphery of each; and
   attaching said inner panty and said outer panty about the waist of the wearer, said inner panty supporting said absorbent pad snugly against the perineal region of the wearer.

* * * * *